(12) United States Patent
Kelly

(10) Patent No.: US 7,153,826 B2
(45) Date of Patent: Dec. 26, 2006

(54) TREATMENT OF ROSACEA

(75) Inventor: Michael T. Kelly, Blaine, WA (US)

(73) Assignee: Seatek Marine Biotechnology, Inc., Vancouver (CA)

( * ) Notice: Subject to any disclaimer, the term of this patent is extended or adjusted under 35 U.S.C. 154(b) by 471 days.

(21) Appl. No.: 10/221,933

(22) PCT Filed: Mar. 19, 2001

(86) PCT No.: PCT/CA01/00358

§ 371 (c)(1),
(2), (4) Date: Dec. 30, 2002

(87) PCT Pub. No.: WO01/68675

PCT Pub. Date: Sep. 20, 2001

(65) Prior Publication Data

US 2004/0023857 A1    Feb. 5, 2004

(30) Foreign Application Priority Data

Mar. 17, 2000 (CA) .................... 2301336

(51) Int. Cl.
*A61K 31/45* (2006.01)
*A61K 38/08* (2006.01)
*A61K 45/06* (2006.01)
*A61P 17/00* (2006.01)
*A61P 17/10* (2006.01)
*A61P 31/00* (2006.01)

(52) U.S. Cl. .............. 514/11; 514/9; 514/24; 514/398

(58) Field of Classification Search .......... None
See application file for complete search history.

(56) References Cited

U.S. PATENT DOCUMENTS

| | | | | |
|---|---|---|---|---|
| 4,510,132 A | * | 4/1985 | Vaara ................. | 514/11 |
| 5,776,919 A | * | 7/1998 | Sukigara et al. ......... | 514/161 |
| 5,998,200 A | * | 12/1999 | Bonaventura et al. ..... | 435/264 |
| 6,509,014 B1 | * | 1/2003 | De Lacharriere et al. ............. | 424/130.1 |
| 6,794,490 B1 | * | 9/2004 | Hill et al. ............. | 530/317 |
| 6,911,525 B1 | * | 6/2005 | Hill et al. ............. | 530/317 |
| 2005/0009747 A1 | * | 1/2005 | Kelleher et al. ......... | 514/12 |

FOREIGN PATENT DOCUMENTS

WO  WO 95/05852 A  3/1995
WO  WO 98/04584 A  2/1998

OTHER PUBLICATIONS

Derwent-Acc-No. 1991-175665. Abstract of RO 99845 A (Sep. 28, 1990).*
BPI: "Rote Liste 1992" Editio Cantor, Autendorf, Germany.
Singer (1998) "Drug therapy of Rosacea: A problem-directed approach" J. Cutan. Med. Surg. 2(Supp 4):S4-20-S4-23.
Gerard, et al., "Loloatin B, A Cyclic Decapeptide Antibiotic Produced in Culture by a Tropical Marine Bacterium" Tetrahedron Letters 37: 7201-7204. (1996).

* cited by examiner

*Primary Examiner*—Jeffrey Edwin Russel
(74) *Attorney, Agent, or Firm*—Townsend and Townsend and Crew LLP

(57) ABSTRACT

Cyclic peptide antibiotics including the loloatins are effective in the treatment of rosacea, particularly when administered in conjunction with an antibiotic such as metronidazole that is effective against anaerobic bacteria.

16 Claims, No Drawings

SEQUENCE LISTING

<160> NUMBER OF SEQ ID NOS: 77

<210> SEQ ID NO 1
<211> LENGTH: 10
<212> TYPE: PRT
<213> ORGANISM: Artificial
<220> FEATURE:
<223> OTHER INFORMATION: Synthetic Peptide

```
<220> FEATURE:
<221> NAME/KEY: MISC_FEATURE
<222> LOCATION: (1)..(1)
<223> OTHER INFORMATION: Xaa = L-valine or butyrine
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (2)..(2)
<223> OTHER INFORMATION: Xaa = L-ornithine or L-diaminobutyric acid
<220> FEATURE:
<221> NAME/KEY: MISC_FEATURE
<222> LOCATION: (3)..(3)
<223> OTHER INFORMATION: Xaa = L-leucine, L-isoleucine,
      L-alloisoleucine, L-norvaline, L-cyclopropylalanine, or norleucine
<220> FEATURE:
<221> NAME/KEY: MISC_FEATURE
<222> LOCATION: (4)..(4)
<223> OTHER INFORMATION: Xaa = D-tyrosine, p-fluorophenylalanine,
      tryptophan, or thienylalanine
<220> FEATURE:
<221> NAME/KEY: MISC_FEATURE
<222> LOCATION: (5)..(5)
<223> OTHER INFORMATION: Xaa = L-proline, azetidine-2-carboxylic acid,
      pipecolic acid, trans-3-methylproline, or trans-4-fluoroproline
<220> FEATURE:
<221> NAME/KEY: MISC_FEATURE
<222> LOCATION: (6)..(6)
<223> OTHER INFORMATION: Xaa = L-phenylalanine, tryptophan, tyrosine,
      p-fluorophenylalanine, thienylalanine, or beta-phenylserine
<220> FEATURE:
<221> NAME/KEY: MISC_FEATURE
<222> LOCATION: (7)..(7)
<223> OTHER INFORMATION: Xaa = D-pheylalanine, tyrosine,
      p-fluorophenylalnine, tryptophan, thienylalanine, or
      beta-phenylserine
<220> FEATURE:
<221> NAME/KEY: MISC_FEATURE
<222> LOCATION: (9)..(9)
<223> OTHER INFORMATION: Xaa = L-aspartic acid or esters thereof
<220> FEATURE:
<221> NAME/KEY: MISC_FEATURE
<222> LOCATION: (10)..(10)
<223> OTHER INFORMATION: Xaa = L-tryptophan, L-tyrosine,
      p-fluorophenylalanine, phenylalanine, thienylalanine,
      beta-phenylserine

<400> SEQUENCE: 1

Xaa Xaa Xaa Xaa Xaa Xaa Xaa Asn Xaa Xaa
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic Peptide - Loloatin A
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (2)..(2)
<223> OTHER INFORMATION: Xaa = L-Orn
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (7)..(7)
<223> OTHER INFORMATION: Xaa = D-Phe
```

-continued

```
<400> SEQUENCE: 2

Val Xaa Leu Xaa Pro Phe Xaa Asn Asp Tyr
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic Peptide - Loloatin B
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (2)..(2)
<223> OTHER INFORMATION: Xaa = L-Orn
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (7)..(7)
<223> OTHER INFORMATION: Xaa = D-Phe

<400> SEQUENCE: 3

Val Xaa Leu Xaa Pro Phe Xaa Asn Asp Trp
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic Peptide - Loloatin C
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (2)..(2)
<223> OTHER INFORMATION: Xaa = L-Orn
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (7)..(7)
<223> OTHER INFORMATION: Xaa = D-Phe

<400> SEQUENCE: 4

Val Xaa Leu Xaa Pro Trp Xaa Asn Asp Trp
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry
```

```
<220> FEATURE:
<221> NAME/KEY: MISC_FEATURE
<222> LOCATION: (2)..(2)
<223> OTHER INFORMATION: Xaa = Orn

<400> SEQUENCE: 5

Val Xaa Leu Tyr Pro Phe Phe Asn Asp Tyr
1               5                   10

<210> SEQ ID NO 6
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry
<220> FEATURE:
<221> NAME/KEY: MISC_FEATURE
<222> LOCATION: (2)..(2)
<223> OTHER INFORMATION: Xaa = Orn

<400> SEQUENCE: 6

Val Xaa Leu Tyr Pro Phe Phe Asn Asp Trp
1               5                   10

<210> SEQ ID NO 7
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry
<220> FEATURE:
<221> NAME/KEY: MISC_FEATURE
<222> LOCATION: (2)..(2)
<223> OTHER INFORMATION: Xaa = Orn

<400> SEQUENCE: 7

Val Xaa Leu Tyr Pro Trp Phe Asn Asp Trp
1               5                   10

<210> SEQ ID NO 8
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
```

```
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = beta-Phenylserine

<400> SEQUENCE: 8

Val Xaa Leu Tyr Pro Trp Phe Asn Asp Xaa
1               5                   10

<210> SEQ ID NO 9
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (2)..(2)
<223> OTHER INFORMATION: Xaa = L-Orn
<220> FEATURE:
<221> NAME/KEY: MISC_FEATURE
<222> LOCATION: (4)..(4)
<223> OTHER INFORMATION: Xaa = D-Tyr
<220> FEATURE:
<221> NAME/KEY: MISC_FEATURE
<222> LOCATION: (7)..(7)
<223> OTHER INFORMATION: Xaa = D-Phe
<220> FEATURE:
<221> NAME/KEY: MISC_FEATURE
<222> LOCATION: (10)..(10)
<223> OTHER INFORMATION: Xaa = L-beta-Phenylserine

<400> SEQUENCE: 9

Val Xaa Leu Xaa Pro Trp Xaa Asn Asp Xaa
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Butyrine
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 10

Xaa Xaa Leu Tyr Pro Phe Phe Asn Asp Tyr
1               5                   10
```

```
<210> SEQ ID NO 11
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Butyrine
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 11

Xaa Xaa Leu Tyr Pro Phe Phe Asn Asp Trp
1               5                   10

<210> SEQ ID NO 12
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa = Butyrine
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 12

Xaa Xaa Leu Tyr Pro Trp Phe Asn Asp Trp
1               5                   10

<210> SEQ ID NO 13
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
```

```
<220> FEATURE:
<221> NAME/KEY: MISC_FEATURE
<222> LOCATION: (2)..(2)
<223> OTHER INFORMATION: Xaa= diaminobutyric acid

<400> SEQUENCE: 13

Val Xaa Leu Tyr Pro Phe Phe Asn Asp Tyr
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = diaminobutyric acid

<400> SEQUENCE: 14

Val Xaa Leu Tyr Pro Phe Phe Asn Asp Trp
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = diaminobutyric acid

<400> SEQUENCE: 15

Val Xaa Leu Tyr Pro Trp Phe Asn Asp Trp
1               5                   10

<210> SEQ ID NO 16
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
```

```
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 16

Val Xaa Ile Tyr Pro Phe Phe Asn Asp Tyr
1               5                   10

<210> SEQ ID NO 17
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 17

Val Xaa Ile Tyr Pro Phe Phe Asn Asp Trp
1               5                   10

<210> SEQ ID NO 18
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 18

Val Xaa Ile Tyr Pro Trp Phe Asn Asp Trp
1               5                   10

<210> SEQ ID NO 19
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Alloisoleucine

<400> SEQUENCE: 19

Val Xaa Xaa Tyr Pro Phe Phe Asn Asp Tyr
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Alloisoleucine

<400> SEQUENCE: 20

Val Xaa Xaa Tyr Pro Phe Phe Asn Asp Trp
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (3)..(3)
<223> OTHER INFORMATION: Xaa = Alloisoleucine

<400> SEQUENCE: 21

Val Xaa Xaa Tyr Pro Trp Phe Asn Asp Trp
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norvaline

<400> SEQUENCE: 22

Val Xaa Xaa Tyr Pro Phe Phe Asn Asp Tyr
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norvaline

<400> SEQUENCE: 23

Val Xaa Xaa Tyr Pro Phe Phe Asn Asp Trp
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norvaline

<400> SEQUENCE: 24

Val Xaa Xaa Tyr Pro Trp Phe Asn Asp Trp
1               5                   10

<210> SEQ ID NO 25
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Cyclopropylalanine

<400> SEQUENCE: 25

Val Xaa Xaa Tyr Pro Phe Phe Asn Asp Tyr
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (3)..(3)
<223> OTHER INFORMATION: Xaa = Cyclopropylalanine

<400> SEQUENCE: 26

Val Xaa Xaa Tyr Pro Phe Phe Asn Asp Trp
1               5                   10

<210> SEQ ID NO 27
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Cyclopropylalanine

<400> SEQUENCE: 27

Val Xaa Xaa Tyr Pro Trp Phe Asn Asp Trp
1               5                   10

<210> SEQ ID NO 28
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norleucine

<400> SEQUENCE: 28

Val Xaa Xaa Tyr Pro Phe Phe Asn Asp Tyr
1               5                   10

<210> SEQ ID NO 29
<211> LENGTH: 10
<212> TYPE: PRT
<213> ORGANISM: Artificial
<220> FEATURE:
<223> OTHER INFORMATION: Synthetic Peptide
```

-continued

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norleucine

<400> SEQUENCE: 29

Val Xaa Xaa Tyr Pro Phe Phe Asn Asp Trp
1               5                   10

<210> SEQ ID NO 30
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (3)..(3)
<223> OTHER INFORMATION: Xaa = Norleucine

<400> SEQUENCE: 30

Val Xaa Xaa Tyr Pro Trp Phe Asn Asp Trp
1               5                   10

<210> SEQ ID NO 31
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (4)..(4)
<223> OTHER INFORMATION: Xaa = p-fluorophenylalanine

<400> SEQUENCE: 31

Val Xaa Leu Xaa Pro Phe Phe Asn Asp Tyr
1               5                   10

<210> SEQ ID NO 32
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (4)..(4)
<223> OTHER INFORMATION: Xaa = p-fluorophenylalanine

<400> SEQUENCE: 32

Val Xaa Leu Xaa Pro Phe Phe Asn Asp Trp
1               5                   10

<210> SEQ ID NO 33
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (4)..(4)
<223> OTHER INFORMATION: Xaa = p-fluorophenylalanine

<400> SEQUENCE: 33

Val Xaa Leu Xaa Pro Trp Phe Asn Asp Trp
1               5                   10

<210> SEQ ID NO 34
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 34

Val Xaa Leu Trp Pro Phe Phe Asn Asp Tyr
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 35

Val Xaa Leu Trp Pro Phe Phe Asn Asp Trp
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 36

Val Xaa Leu Trp Pro Trp Phe Asn Asp Trp
1               5                   10

<210> SEQ ID NO 37
<211> LENGTH: 10
<212> TYPE: PRT
<213> ORGANISM: Artificial
```

-continued

```
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (4)..(4)
<223> OTHER INFORMATION: Xaa = Thienylalanine

<400> SEQUENCE: 37

Val Xaa Leu Xaa Pro Phe Phe Asn Asp Tyr
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (4)..(4)
<223> OTHER INFORMATION: Xaa = Thienylalanine

<400> SEQUENCE: 38

Val Xaa Leu Xaa Pro Phe Phe Asn Asp Trp
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (4)..(4)
<223> OTHER INFORMATION: Xaa = Thienylalanine

<400> SEQUENCE: 39

Val Xaa Leu Xaa Pro Trp Phe Asn Asp Trp
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = Azetidine-2-carboxylic acid

<400> SEQUENCE: 40

Val Xaa Leu Tyr Xaa Phe Phe Asn Asp Tyr
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = Azetidine-2-carboxylic acid

<400> SEQUENCE: 41

Val Xaa Leu Tyr Xaa Phe Phe Asn Asp Trp
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = Azetidine-2-carboxylic acid

<400> SEQUENCE: 42

Val Xaa Leu Tyr Xaa Trp Phe Asn Asp Trp
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = Pipecolic Acid

<400> SEQUENCE: 43

Val Xaa Leu Tyr Xaa Phe Phe Asn Asp Tyr
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (5)..(5)
<223> OTHER INFORMATION: Xaa = Pipecolic acid

<400> SEQUENCE: 44

Val Xaa Leu Tyr Xaa Phe Phe Asn Asp Trp
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = Pipecolic acid

<400> SEQUENCE: 45

Val Xaa Leu Tyr Xaa Trp Phe Asn Asp Trp
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = trans-3-Methylproline

<400> SEQUENCE: 46

Val Xaa Leu Tyr Xaa Phe Phe Asn Asp Tyr
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = trans-3-Methylproline

<400> SEQUENCE: 47

Val Xaa Leu Tyr Xaa Phe Phe Asn Asp Trp
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = trans-3-Methylproline

<400> SEQUENCE: 48

Val Xaa Leu Tyr Xaa Trp Phe Asn Asp Trp
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (5)..(5)
<223> OTHER INFORMATION: Xaa = trans4-Fluoroproline

<400> SEQUENCE: 49

Val Xaa Leu Tyr Xaa Phe Phe Asn Asp Tyr
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = trans4-Fluoroproline

<400> SEQUENCE: 50

Val Xaa Leu Tyr Xaa Phe Phe Asn Asp Trp
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (5)..(5)
<223> OTHER INFORMATION: Xaa = trans4-Fluoroproline

<400> SEQUENCE: 51

Val Xaa Leu Tyr Xaa Trp Phe Asn Asp Trp
1               5                   10

<210> SEQ ID NO 52
<211> LENGTH: 10
<212> TYPE: PRT
<213> ORGANISM: Artificial
```

```
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 52

Val Xaa Leu Tyr Pro Tyr Phe Asn Asp Tyr
1               5                   10

<210> SEQ ID NO 53
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 53

Val Xaa Leu Tyr Pro Tyr Phe Asn Asp Trp
1               5                   10

<210> SEQ ID NO 54
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (6)..(6)
<223> OTHER INFORMATION: Xaa = p-fluorophenylalanine

<400> SEQUENCE: 54

Val Xaa Leu Tyr Pro Xaa Phe Asn Asp Tyr
1               5                   10
```

```
<210> SEQ ID NO 55
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (6)..(6)
<223> OTHER INFORMATION: Xaa = p-Fluorophenylalanine

<400> SEQUENCE: 55

Val Xaa Leu Tyr Pro Xaa Phe Asn Asp Trp
1               5                   10

<210> SEQ ID NO 56
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 56

Val Xaa Leu Tyr Pro Trp Phe Asn Asp Tyr
1               5                   10

<210> SEQ ID NO 57
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
```

```
<220> FEATURE:
<221> NAME/KEY: MISC_FEATURE
<222> LOCATION: (6)..(6)
<223> OTHER INFORMATION: Xaa = Thienylalanine

<400> SEQUENCE: 57

Val Xaa Leu Tyr Pro Xaa Phe Asn Asp Tyr
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (6)..(6)
<223> OTHER INFORMATION: Xaa = Thienylalanine

<400> SEQUENCE: 58

Val Xaa Leu Tyr Pro Xaa Phe Asn Asp Trp
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (6)..(6)
<223> OTHER INFORMATION: Xaa = beta-Phenylserine

<400> SEQUENCE: 59

Val Xaa Leu Tyr Pro Xaa Phe Asn Asp Tyr
1               5                   10

<210> SEQ ID NO 60
<211> LENGTH: 10
<212> TYPE: PRT
<213> ORGANISM: Artificial
<220> FEATURE:
<223> OTHER INFORMATION: Synthetic Peptide
```

```
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (6)..(6)
<223> OTHER INFORMATION: Xaa = beta-Phenylserine

<400> SEQUENCE: 60

Val Xaa Leu Tyr Pro Xaa Phe Asn Asp Trp
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 61

Val Xaa Leu Tyr Pro Phe Tyr Asn Asp Tyr
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 62

Val Xaa Leu Tyr Pro Phe Tyr Asn Asp Trp
1               5                   10
```

```
<210> SEQ ID NO 63
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = p-Fluorophenylalanine

<400> SEQUENCE: 63

Val Xaa Leu Tyr Pro Phe Xaa Asn Asp Tyr
1               5                   10

<210> SEQ ID NO 64
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = p-Fluorophenylalanine

<400> SEQUENCE: 64

Val Xaa Leu Tyr Pro Phe Xaa Asn Asp Trp
1               5                   10

<210> SEQ ID NO 65
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
```

```
<220> FEATURE:
<221> NAME/KEY: MISC_FEATURE
<222> LOCATION: (2)..(2)
<223> OTHER INFORMATION: Xaa = Orn

<400> SEQUENCE: 65

Val Xaa Leu Tyr Pro Phe Trp Asn Asp Tyr
1               5                   10

<210> SEQ ID NO 66
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 66

Val Xaa Leu Tyr Pro Phe Trp Asn Asp Trp
1               5                   10

<210> SEQ ID NO 67
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = Thienylalanine

<400> SEQUENCE: 67

Val Xaa Leu Tyr Pro Phe Xaa Asn Asp Tyr
1               5                   10

<210> SEQ ID NO 68
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
```

```
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = Thienylalanine

<400> SEQUENCE: 68

Val Xaa Leu Tyr Pro Phe Xaa Asn Asp Trp
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = beta-Phenylserine

<400> SEQUENCE: 69

Val Xaa Leu Tyr Pro Phe Xaa Asn Asp Tyr
1               5                   10

<210> SEQ ID NO 70
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (7)..(7)
<223> OTHER INFORMATION: Xaa = beta-Phenylserine
```

```
<400> SEQUENCE: 70

Val Xaa Leu Tyr Pro Phe Xaa Asn Asp Trp
1               5                   10

<210> SEQ ID NO 71
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = p-Fluorophenylalanine

<400> SEQUENCE: 71

Val Xaa Leu Tyr Pro Phe Phe Asn Asp Xaa
1               5                   10

<210> SEQ ID NO 72
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = p-Fluorophenylalanine

<400> SEQUENCE: 72

Val Xaa Leu Tyr Pro Trp Phe Asn Asp Xaa
1               5                   10

<210> SEQ ID NO 73
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
```

```
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 73

Val Xaa Leu Tyr Pro Phe Phe Asn Asp Phe
1               5                   10

<210> SEQ ID NO 74
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn

<400> SEQUENCE: 74

Val Xaa Leu Tyr Pro Trp Phe Asn Asp Phe
1               5                   10

<210> SEQ ID NO 75
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = Thienylalanine

<400> SEQUENCE: 75

Val Xaa Leu Tyr Pro Phe Phe Asn Asp Xaa
1               5                   10

<210> SEQ ID NO 76
<211> LENGTH: 10
<212> TYPE: PRT
<213> ORGANISM: Artificial
```

```
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = Thienylalanine

<400> SEQUENCE: 76

Val Xaa Leu Tyr Pro Trp Phe Asn Asp Xaa
1               5                   10

<210> SEQ ID NO 77
<211> LENGTH: 10
<212> TYPE: PRT
<213> ORGANISM: Artificial
<220> FEATURE:
<223> OTHER INFORMATION: Synthetic Peptide
<220> FEATURE:
<221> NAME/KEY: MISC_FEATURE
<222> LOCATION: (1)..(10)
<223> OTHER INFORMATION: Cyclic Peptide
<220> FEATURE:
<221> NAME/KEY: MISC_FEATURE
<222> LOCATION: (1)..(10)
<223> OTHER INFORMATION: Each amino acid may have L-form or D-form
      stereochemistry with preferred analogs having the sterochemistry
      L-, L-, L-, D-, L-, L-, D-, L-, L-, and L-
<220> FEATURE:
<221> NAME/KEY: MISC_FEATURE
<222> LOCATION: (2)..(2)
<223> OTHER INFORMATION: Xaa = Orn
<220> FEATURE:
<221> NAME/KEY: MISC_FEATURE
<222> LOCATION: (10)..(10)
<223> OTHER INFORMATION: Xaa = beta-Phenylserine

<400> SEQUENCE: 77

Val Xaa Leu Tyr Pro Phe Phe Asn Asp Xaa
1               5                   10
```

TREATMENT OF ROSACEA

TECHNICAL FIELD

This invention relates to the use of antibiotics for treatment of rosacea.

BACKGROUND OF THE INVENTION

Rosacea is a chronic dermatologic disease which typically develops in middle aged adults. Presentation varies from redness and flushing of the checks early in the disease to red, painful nodules as the disease progresses. The nodules may develop into papules and pustules. The disease progressively leads to scarring, vascularization and in some cases, swelling of the face. The effect on the nose may be especially severe, resulting in rhinophyma, a disfiguring, bluish enlargement of the nose. Rhinophyma requires surgery for correction. Once rosacea develops, it is typically present for life.

The etiology of rosacea is unknown. Some antibiotics have been used for systemic and topical treatment of rosacea. However, it is unknown whether such antibiotics treat the cause of the disease or a secondary bacterial or fungal infection at the site of lesions. It is also unknown whether the effect of antibiotics is due to a general anti-inflammatory effect. Some antibiotics (e.g. tetracycline) are ineffective when applied topically but somewhat effective when administered systemically. All known antibiotic treatments for rosacea are suppressive, rather than curative.

Rosacea treatment with topical antibiotics is long-term, usually carried out for life. The current therapy of choice is metronidazole administered topically twice daily. A 0.75% wt metronidazole medicament often used in this treatment is sold under the trademark MetroGel. However, metronidazole is only partially effective. It has an affect on papules and pustules but is generally ineffective against skin redness, telangiectases or flushing. Overall, about 50% of patients do not benefit from metronidazole treatment. The remaining patients respond initially but experience reduced effectiveness from the treatment over time. Accordingly, a need exists for more effective treatment of rosacea.

SUMMARY OF THE INVENTION

The inventor has determined that cyclic peptide antibiotics are particularly effective in the treatment of rosacea.

This invention provides the use of a cyclic peptide antibiotic or a pharmaceutically acceptable salt thereof for the preparation of a medicament for the treatment of rosacea.

This invention provides the use of a first antibiotic in the topical treatment of rosacea or for preparation of a medicament for topical administration in the treatment of rosacea, wherein the first antibiotic is a cyclic peptide. Preferably, such use will be in conjunction with the use of a second antibiotic which is at least partially effective in the topical treatment of rosacea. Preferably, the first antibiotic will be a loloatin, as defined herein. Preferably, the second antibiotic will be an antibiotic effective against anaerobic bacteria, e.g. metronidazole. The first and second antibiotics may be present in the same composition or formulation for topical administration or may be present in separate formulations or compositions. The first and second antibiotics may be administered simultaneously or close in time or the antibiotics may be administered at different times.

This invention provides a method for the treatment of a patient afflicted with rosacea comprising topical administration to the patient of a therapeutically effective amount of a cyclic peptide antibiotic or a pharmaceutically acceptable salt thereof. In this method, administration will typically be to a site of presentation of rosacea, including areas of redness, flushing, nodules, papules or pustules on the skin of the patient afflicted with rosacea. Preferably, administration will be done to both affected and surrounding unaffected areas. Therefore, administration may be to the entirety of the patient's face or neck or both the face and neck. This method may additionally comprise administration of a therapeutically effective amount of a second antibiotic (which second antibiotic may only be partially effective in the treatment of rosacea) in the same manner as for the cyclic peptide antibiotic. Thus, the second antibiotic may only be "at least partially effective" in the treatment of rosacea. Preferably, the second antibiotic will be effective against an anaerobic bacterium.

This invention also provides pharmaceutical compositions suitable for topical administration for the treatment of rosacea, comprising: a cyclic peptide antibiotic or pharmaceutically acceptable salt thereof; an antibiotic or pharmaceutically acceptable salt thereof effective against an anaerobic bacterium; and, a carrier.

Administration of a cyclic peptide antibiotic significantly improves treatment of rosacea. Furthermore, such antibiotics are more resistant to proteolysis than linear peptides and can be effective against antibiotic resistant bacteria. The results of treatment with a cyclic peptide antibiotic in conjunction with an antibiotic known to be at least partially effective against rosacea and anaerobic bacteria (e.g. metronidazole) is much better as compared to only the use of previously described antibiotics. This may be because in some cases, rosacea appears to involve an abnormal inflammatory response to multiple bacterial infections, for example by a *Staphylococcus* species and an anaerobic *bacterium* such as *Propionibacterium* acnes. Metronidazole would be effective against such an anaerobic *bacterium* but not against *Staphylococcus*.

DETAILED DESCRIPTION OF THE INVENTION

While this invention is susceptible to embodiment in many different forms, preferred embodiments of the invention will be described in detail. The following description is an exemplification of the principles of this invention and is not intended to limit the invention to the embodiments illustrated.

Any reference herein to a "cyclic peptide" antibiotic encompasses cyclic peptides suitable for topical administration to a patient and which demonstrate therapeutically useful activity against bacteria. Such antibiotics include but are not limited to the cyclic peptide antibiotics known generically as: cyclic gramicidins (e.g. gramicidin S); tyrocidins (e.g. tyrocidin A, B, and C); tyrothricins (e.g. mixtures of linear or cyclic gramicidins and tyrocidins); and, loloatins (e.g. loloatin A, B, and C).

Cyclic peptide antibiotics, which are particularly effective against resistant bacteria and are preferred for use in this invention are those antibiotics known generically as loloatins, which term includes loloatin A, B and C, their derivatives and analogs as described in Gerard, J. et al. (1996) Tetrahedron Letters 37:7201–7204; International Patent Application published Feb. 5, 1998 under WO 98/04584; and in U.S. Pat. No. 5,962,407 issued Oct. 5, 1999.

The term "treatment" as used herein means alleviation of symptoms of a disease condition. The term "effective" as used herein with respect to an agent used against a bacterium means that the agent is capable of reducing the presence of such bacteria at a site of infection or is capable of reducing the occurrence of an infection by such bacteria. The term "partially effective" as used herein with respect to an agent used in the treatment of rosacea means that the agent is effective in only a portion of patients, or lacks the ability to substantially alleviate symptoms of the disease or lacks the ability to control the disease over time.

Loloatins are cyclic decapeptide compounds as represented by the structure shown below, denoted Formula (A):

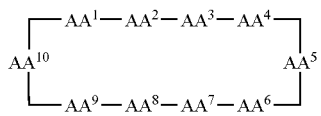

In Formula (A), $AA_1$ through $AA_{10}$ are generic symbols, each representing an amino acid residue as defined herein, or a salt or derivative thereof. Each line between neighboring (attached) $AA_1$–$AA_{10}$ residues represents an amide (also known as a peptide) bond formed between neighboring $AA.sup_1$–$AA_{10}$ residues, as well as the isosteres thereof. "Isostere" means a modified form of the normal peptide bond (—C(O)NH—) between attached amino acid residues, such as —$CH_2$ NH— (reduced), C(O)N($CH_3$) (N-methylamide), —$COCH_2$— (keto), —CH(OH)$CH_2$— (hydroxy), —CH($NH_2$)$CH_2$— (amino), —$CH_2$ $CH_2$— (hydrocarbon), or —NHC(O)— (inverted normal peptide bond). Preferably the compounds are not in isosteric forms.

In Formula (A), $AA_1$–$AA_{10}$ represent residues from the following specific amino acids or other listed compounds, where stereochemical designations are preferred only, and the specifically named amino acid or other listed compound may be in either the L or D form:

AA.1: L-valine, butyrine;
AA.2: L-ornithine, L-diaminobutyric acid;
AA.3: L-leucine, L-isoleucine, L-alloisoleucine, L-norvaline, L-cyclopropylalanine, norleucine;
AA.4: D-tyrosine, p-fluorophenylalanine, tryptophan, thienylalanine;
AA.5: L-proline, azetidine-2-carboxylic acid, pipecolic acid, trans-3-methylproline, trans-4-fluoroproline;
AA.6: L-phenylalanine, tryptophan, tyrosine, p-fluorophenylalanine, thienylalanine, .β.-phenylserine;
AA.7: D-phenylalanine, tyrosine, p-fluorophenylalanine, tryptophan, thienylalanine, .β. -phenylserine;
AA.8: L-asparagine;
AA.9: L-aspartic acid or esters thereof; and
AA. 10: L-tryptophan, L-tyrosine, p-fluorophenylalanine, phenylalanine, thienylalanine, .β. -phenylserine.

The above formula describes SEQ ID NO: 1.

The compounds of Formula (A) include salts and other derivatives of the amino acids listed above. An amino acid derivative is intended to include the solvates, salts (either acid- or base- addition salts, depending on whether the amino acid sidechain is basic or acidic, respectively), esters (derivatives of amino acid sidechains containing a carboxylic acid group), amines (derivatives of amino acid sidechains containing an amino group), ethers (derivatives of amino acid sidechains containing an hydroxyl group) and amides (derivatives of amino acid sidechains containing either an amine or carboxylic acid group) of the unmodified cyclic compound.

The recitation of Formula (A) is intended to denote all possible isomers within the structural formula, in particular optical isomers. Also included are mixtures of isomers, and individual isomers, including racemic mixtures, where they can be resolved.

Also included are esters of the compounds of Formula (A). In particular, the recitation of an amino acid residue having a carboxylic acid group is to be regarded as a recitation of all possible esters of that carboxylic acid. Compounds having phenolic groups are to be regarded as covering all possible ethers or esters of the phenolic hydroxyl group.

Loloatins A, B and C may be represented by the following formulae:
cyclo[L-Val-L-Orn-L-Leu-D-Tyr-L-Pro-L-Phe-D-Phe-L-Asn-L-Asp-L-Tyr] (Loloatin A; SEQ ID NO:2)
cyclo[L-Val-L-Orn-L-Leu-D-Tyr-L-Pro-L-Phe-D-Phe-L-Asn-L-Asp-L-Trp] (Loloatin B; SEQ ID NO:3); and
cyclo[L-Val-L-Orn-L-Leu-D-Tyr-L-Pro-L-Trp-D-Phe-L-Asn-L-Asp-L-Trp] (Loloatin C; SEQ ID NO:4).

Loloatin analogs include cyclic decapeptides having a "non-natural" stereochemistry at one or more of the .alpha.-carbons of the component amino acids, where the "natural" stereochemistry is as indicated by the L- or D-designations preceding the name of each of the amino acids in the formulas for Loloatin A, B and C set forth above. Collectively, Loloatin A, B, and C and their analogs having "non-natural" stereochemistry are represented by the formulae:
cyclo[Val-Orn-Leu-Tyr-Pro-Phe-Phe-Asn-Asp-Tyr] (SEQ ID NO:5);
cyclo[Val-Orn-Leu-Tyr-Pro-Phe-Phe-Asn-Asp-Trp] (SEQ ID NO:6); and,
cyclo[Val-Orn-Leu-Tyr-Pro-Trp-Phe-Asn-Asp-Trp] (SEQ ID NO:7).

Furthermore, this invention includes use of various analogs of the above-identified compounds, where preferred analogs have the formulas listed below. In the below-listed structures, no stereochemistry is designated because the analogs may have any possible sereochemistry at each atom capable of having more than one stereochemical arrangement of substituents. However, looking at the below listed sequences from left to right as written, preferred analogs have the stereochemistry L-, L-, L-, D-, L-, L-, D-, L, L- and L-. For example, cyclo[Val-Orn-Leu-Tyr-Pro-Trp-Phe-Asn-Asp-.β.-Phenylserine] (SEQ ID NO:8) as written below preferably has the stereochemistry cyclo[L-Val-L-Orn-L-Leu-D-Tyr-L-Pro-L-Trp-D-Phe-L-Asn-L-Asp-L-.β.-Phenylserine] (SEQ ID NO:9).

Preferred analogs have one amino acid residue present in Loloatin A, B or C replaced with a different amino acid residue. Preferred analogs are:
cyclo[Butyrine-Orn-Leu-Tyr-Pro-Phe-Phe-Asn-Asp-Tyr] (SEQ ID NO:10);
cyclo[Butyrine-Orn-Leu-Tyr-Pro-Phe-Phe-Asn-Asp-Trp] (SEQ ID NO:11);
cyclo[Butyrine-Orn-Leu-Tyr-Pro-Trp-Phe-Asn-Asp-Trp] (SEQ ID NO:12);
cyclo[Val-diaminobutyric acid-Leu-Tyr-Pro-Phe-Phe-Asn-Asp-Tyr] (SEQ ID NO:13);
cyclo[Val-diaminobutyric acid-Leu-Tyr-Pro-Phe-Phe-Asn-Asp-Trp] (SEQ ID NO:14);
cyclo[Val-diaminobutyric acid-Leu-Tyr-Pro-Trp-Phe-Asn-Asp-Trp] (SEQ ID NO:15);
cyclo[Val-Orn-Isoleucine-Tyr-Pro-Phe-Phe-Asn-Asp-Tyr] (SEQ ID NO:16);

cyclo[Val-Orn-Isoleucine-Tyr-Pro-Phe-Phe-Asn-Asp-Trp] (SEQ ID NO:17);
cyclo[Val-Orn-Isoleucine-Tyr-Pro-Trp-Phe-Asn-Asp-Trp] (SEQ ID NO:18);
cyclo[Val-Orn-Alloisoleucine-Tyr-Pro-Phe-Phe-Asn-Asp-Tyr] (SEQ ID NO:19);
cyclo[Val-Orn-Alloisoleucine-Tyr-Pro-Phe-Phe-Asn-Asp-Trp] (SEQ ID NO:20);
cyclo[Val-Orn-Alloisoleucine-Tyr-Pro-Trp-Phe-Asn-Asp-Trp] (SEQ ID NO:21);
cyclo[Val-Orn-Norvaline-Tyr-Pro-Phe-Phe-Asn-Asp-Tyr] (SEQ ID NO:22);
cyclo[Val-Orn-Norvaline-Tyr-Pro-Phe-Phe-Asn-Asp-Trp] (SEQ ID NO:23);
cyclo[Val-Orn-Norvaline-Tyr-Pro-Trp-Phe-Asn-Asp-Trp] (SEQ ID NO:24);
cyclo[Val-Orn-Cyclopropylalanine-Tyr-Pro-Phe-Phe-Asn-Asp-Tyr] (SEQ ID NO:25);
cyclo[Val-Orn-Cyclopropylalanine-Tyr-Pro-Phe-Phe-Asn-Asp-Trp] (SEQ ID NO:26);
cyclo[Val-Orn-Cyclopropylalanine-Tyr-Pro-Trp-Phe-Asn-Asp-Trp] (SEQ ID NO:27);
cyclo[Val-Orn-Norleucine-Tyr-Pro-Phe-Phe-Asn-Asp-Tyr] (SEQ ID NO:28);
cyclo[Val-Orn-Norleucine-Tyr-Pro-Phe-Phe-Asn-Asp-Trp] (SEQ ID NO:29);
cyclo[Val-Orn-Norleucine-Tyr-Pro-Trp-Phe-Asn-Asp-Trp] (SEQ ID NO:30);
cyclo[Val-Orn-Leu-p-fluorophenylalanine-Pro-Phe-Phe-Asn-Asp-Tyr] (SEQ ID NO:31);
cyclo[Val-Orn-Leu-p-fluorophenylalanine-Pro-Phe-Phe-Asn-Asp-Trp] (SEQ ID NO:32);
cyclo[Val-Orn-Leu-p-fluorophenylalanine-Pro-Trp-Phe-Asn-Asp-Trp] (SEQ ID NO:33);
cyclo[Val-Orn-Leu-Tryptophan-Pro-Phe-Phe-Asn-Asp-Tyr] (SEQ ID NO:34);
cyclo[Val-Orn-Leu-Tryptophan-Pro-Phe-Phe-Asn-Asp-Trp] (SEQ ID NO:35);
cyclo[Val-Orn-Leu-Tryptophan-Pro-Trp-Phe-Asn-Asp-Trp] (SEQ ID NO:36);
cyclo[Val-Orn-Leu-Thienylalanine-Pro-Phe-Phe-Asn-Asp-Tyr] (SEQ ID NO:37);
cyclo[Val-Orn-Leu-Thienylalanine-Pro-Phe-Phe-Asn-Asp-Trp] (SEQ ID NO:38);
cyclo[Val-Orn-Leu-Thienylalanine-Pro-Trp-Phe-Asn-Asp-Trp] (SEQ ID NO:39);
cyclo[Val-Orn-Leu-Tyr-Azetidine-2-carboxylic acid-Phe-Phe-Asn-Asp-Tyr] (SEQ ID NO:40);
cyclo[Val-Orn-Leu-Tyr-Azetidine-2-carboxylic acid-Phe-Phe-Asn-Asp-Trp] (SEQ ID NO:41);
cyclo[Val-Orn-Leu-Tyr-Azetidine-2-carboxylic acid-Trp-Phe-Asn-Asp-Trp] (SEQ ID NO:42);
cyclo[Val-Orn-Leu-Tyr-Pipecolic acid-Phe-Phe-Asn-Asp-Tyr] (SEQ ID NO:43);
cyclo[Val-Orn-Leu-Tyr-Pipecolic acid-Phe-Phe-Asn-Asp-Trp] (SEQ ID NO:44);
cyclo[Val-Orn-Leu-Tyr-Pipecolic acid-Trp-Phe-Asn-Asp-Trp] (SEQ ID NO:45);
cyclo[Val-Orn-Leu-Tyr-trans-3-Methylproline-Phe-Phe-Asn-Asp-Tyr] (SEQ ID NO:46);
cyclo[Val-Orn-Leu-Tyr-trans-3-Methylproline-Phe-Phe-Asn-Asp-Trp] (SEQ ID NO:47);
cyclo[Val-Orn-Leu-Tyr-trans-3-Methylproline-Trp-Phe-Asn-Asp-Trp] (SEQ ID NO:48);
cyclo[Val-Orn-Leu-Tyr-trans4-Fluoroproline-Phe-Phe-Asn-Asp-Tyr] (SEQ ID NO:49);
cyclo[Val-Orn-Leu-Tyr-trans4-Fluoroproline-Phe-Phe-Asn-Asp-Trp] (SEQ ID NO:50);
cyclo[Val-Orn-Leu-Tyr-trans4-Fluoroproline-Trp-Phe-Asn-Asp-Trp] (SEQ ID NO:51);
cyclo[Val-Orn-Leu-Tyr-Pro-Tyr-Phe-Asn-Asp-Tyr] (SEQ ID NO:52);
cyclo[Val-Orn-Leu-Tyr-Pro-Tyr-Pher-Asn-Asp-Trp] (SEQ ID NO:53);
cyclo[Val-Orn-Leu-Tyr-Pro-p-Fluorophenylalanine-Phe-Asn-Asp-Tyr] (SEQ ID NO:54);
cyclo[Val-Orn-Leu-Tyr-Pro-p-Fluorophenylalanine-Phe-Asn-Asp-Trp] (SEQ ID NO:55);
cyclo[Val-Orn-Leu-Tyr-Pro-Trp-Phe-Asn-Asp-Tyr] (SEQ ID NO:56);
cyclo[Val-Orn-Leu-Tyr-Pro-Trp-Phe-Asn-Asp-Trp] (SEQ ID NO:7);
cyclo[Val-Orn-Leu-Tyr-Pro-Thienylalanine-Phe-Asn-Asp-Tyr] (SEQ ID NO:57);
cyclo[Val-Orn-Leu-Tyr-Pro-Thienylalanine-Phe-Asn-Asp-Trp] (SEQ ID NO:58);
cyclo[Val-Orn-Leu-Tyr-Pro-..beta..-Phenylserine-Phe-Asn-Asp-Tyr] (SEQ ID NO:59);
cyclo[Val-Orn-Leu-Tyr-Pro-..beta..-Phenylserine-Phe-Asn-Asp-Trp] (SEQ ID NO:60);
cyclo[Val-Orn-Leu-Tyr-Pro-Phe-Tyr-Asn-Asp-Tyr] (SEQ ID NO:61);
cyclo[Val-Orn-Leu-Tyr-Pro-Phe-Tyr-Asn-Asp-Trp] (SEQ ID NO:62);
cyclo[Val-Orn-Leu-Tyr-Pro-Phe-p-Fluorophenylalanine-Asn-Asp-Tyr] (SEQ ID NO:63);
cyclo[Val-Orn-Leu-Tyr-Pro-Phe-p-Fluorophenylalanine-Asn-Asp-Trp] (SEQ ID NO:64);
cyclo[Val-Orn-Leu-Tyr-Pro-Phe-Trp-Asn-Asp-Tyr] (SEQ ID NO:65);
cyclo[Val-Orn-Leu-Tyr-Pro-Phe-Trp-Asn-Asp-Trp] (SEQ ID NO:66);
cyclo[Val-Orn-Leu-Tyr-Pro-Phe-Thienylalanine-Asn-Asp-Tyr] (SEQ ID NO:67);
cyclo[Val-Orn-Leu-Tyr-Pro-Phe-Thienylalanine-Asn-Asp-Trp] (SEQ ID NO:68);
cyclo[Val-Orn-Leu-Tyr-Pro-Phe-..beta..-Phenylserine-Asn-Asp-Tyr] (SEQ ID NO:69);
cyclo[Val-Orn-Leu-Tyr-Pro-Phe-..beta..-Phenylserine-Asn-Asp-Trp] (SEQ ID NO:70);
cyclo[Val-Orn-Leu-Tyr-Pro-Phe-Phe-Asn-Asp-p-Fluorophenylalanine] (SEQ ID NO:71);
cyclo[Val-Orn-Leu-Tyr-Pro-Trp-Phe-Asn-Asp-p-Fluorophenylalanine] (SEQ ID NO:72);
cyclo[Val-Orn-Leu-Tyr-Pro-Phe-Phe-Asn-Asp-Phe] (SEQ ID NO:73);
cyclo[Val-Orn-Leu-Tyr-Pro-Trp-Phe-Asn-Asp-Phe] (SEQ ID NO:74);
cyclo[Val-Orn-Leu-Tyr-Pro-Phe-Phe-Asn-Asp-Thienylalanine] (SEQ ID NO:75);
cyclo[Val-Orn-Leu-Tyr-Pro-Trp-Phe-Asn-Asp-Thienylalanine] (SEQ ID NO:76);
cyclo[Val-Orn-Leu-Tyr-Pro-Phe-Phe-Asn-Asp-..beta..-Phenylserine] (SEQ ID NO:77); and
cyclo[Val-Orn-Leu-Tyr-Pro-Trp-Phe-Asn-Asp-..beta..-Phenylserine] (SEQ ID NO:8).

Loloatin A, B, and C as well as derivatives and analogs thereof may be obtained or synthesized according to methods as described in the art.

Other cyclic peptide antibiotics may be determined from the prior art. Such antibiotics, when administered topically, will demonstrate relief from bacterial infections on the skin. Such relief refers to a decrease in severity over that expected in the absence of treatment and does not necessarily indicate a total elimination of the infection.

In determining a therapeutically effective amount or dose, a number of factors will be considered by the attending diagnostician, including but not limited to: the species of animal being treated, its size, age, and general health, the specific infection involved, the degree of or involvement or the severity of the infection or condition arising therefrom, the response of an individual patient, the particular compound administered, the bioavailability characteristics of the preparation administered; the dose regime selected; the use of concomitant medication; and other relevant circumstances.

Antibiotics which are at least partially effective in the topical treatment of rosacea and may be employed for use in this invention as a "second antibiotic" are antibiotics which provide at least some relief (are at least partially effective) in the treatment of rosacea when topically administered. These antibiotics are preferably ones which are effective against anaerobic bacteria, such as clindamycin and metronidazole. The most preferred compound for use as the "second antibiotic" is metronidazole, which is commercially available in various topical formulations.

Antibiotics effective for use in this invention are typically administered topically in a pharmaceutical composition (medicament) comprising a suitable carrier. Such a carrier may comprise a solution, ointment, gel-base, or the like. Such a carrier may comprise one or more of the following: petrolatum, lanolin, polyethylene glycols, bee wax, paraffin, mineral oil, diluents such as water or alcohol, emulsifiers and stabilizers. Formulations for pharmaceutical compositions of this invention for topical administration may contain from about 0.1 to about 10% weight per unit volume active ingredient but formulations outside this range may be acceptable. Such formulations may contain solutions or suspensions of the antibiotics and include one or more adjuncts, diluents such as sterile water or saline solution, alcohol, fixed oils, polyethylene glycols, glycerin, propylene glycol, or other synthetic solvents. Where possible, aqueous diluents or suspensions are preferred in view of typical long-term use of topical formulations for treatment of rosacea. For the same reason, topical formulations designed as skin care products which promote the softening of skin and/or screening of sunlight may be preferred for such long-term use.

Pharmaceutical compositions (medicaments) for use in this invention will typically be applied directly to the sites of rosacea lesions, including areas of redness, pustules, etc. as well as surrounding unaffected areas on the face and neck of a patient. The quantity to be applied per treatment and the frequency of treatments may be readily determined by the diagnostician.

The therapeutic effectiveness of the present invention is demonstrated in the following examples which are meant to illustrate the invention rather than to limit its scope.

EXAMPLE 1

The effectiveness of a cyclic decapeptide antibiotic for treating rosacea was determined on a human subject afflicted, for two years duration, with moderately severe rosacea and pustular lesions. The subject had undergone previous treatments with metronidazole without benefit. The subject received topical metronidazole in a carbomer gel composition (Metrogel™) applied in the morning. Topical loloatin B (which was obtained by fermentation of the Bacillus deposited as ATCC 55797 generally following the methods described in WO98/04584) was applied in the evening. The loloatin was first dissolved in a minimal amount of alcohol which was then mixed with Lubriderm™ lotion to provide 1% w/v formulation. Significant improvement in the rosacea was observed after one month of this treatment regimen. When the loloatin was omitted from the regimen and Metrogel™ applied twice daily, the rosacea returned within one week. Each time the regimen of once daily Metrogel™ and once daily loloatin was reinstituted, significant improvement in the rosacea was observed.

EXAMPLE 2

A subject afflicted with rosacea received topical Metrogel™ overlayed with Lubriderm™ lotion in the morning and 1% loloatin B formulated in Lubriderm™ (as described above) in the evening. Progressive improvement of the rosacea took place and the condition was effectively controlled throughout the trial period (two years). With this combined treatment, the rosacea was controlled such that only a few lesions were present at any given time, and complete remissions of several days duration became common. This combined treatment also reduced the healing time of the lesions from six months with Metrogel™ treatment alone, to within 2–3 days.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims. All patents, patent applications and publications referred to herein are hereby incorporated by reference.

What is claimed is:

1. A pharmaceutical composition for use in the treatment of rosacea, comprising: a carrier suitable for topical administration; at least one cyclic peptide antibiotic or a pharmaceutically acceptable salt thereof; and, at least one additional antibiotic or pharmaceutically acceptable salt thereof, wherein the additional antibiotic is effective against an anaerobic bacterium, wherein the cyclic peptide antibiotic is selected from the group consisting of: loloatins; cyclic gramicidins; tyrocidins; and tyrothricins.

2. The composition of claim 1, wherein the cyclic peptide antibiotic is a loloatin.

3. The composition of claim 1, wherein the cyclic peptide antibiotic or pharmaceutically acceptable salt thereof is a compound of Formula (A)

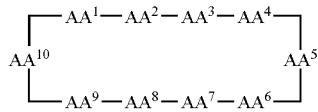

wherein $AA_1$ through $AA_{10}$ are generic symbols, each representing an amino acid residue, a salt or a derivative thereof, and each line between $AA_1$ through $AA_{10}$ represents an amide bond or an isostere thereof.

4. A pharmaceutical composition for use in the treatment of rosacea, comprising: a carrier suitable for topical administration; at least one cyclic peptide antibiotic or a pharmaceutically acceptable salt thereof; and, at least one additional antibiotic or pharmaceutically acceptable salt thereof, wherein the additional antibiotic is effective against an anaerobic *bacterium*, wherein the cyclic peptide antibiotic is selected from the group consisting of:

cyclo[Val-Orn-Leu-Tyr-Pro-Phe-Phe-Asn-Asp-Tyr] (SEQ ID NO:5);
cyclo[Val-Orn-Leu-Tyr-Pro-Phe-Phe-Asn-Asp-Trp] (SEQ ID NO:6);
cyclo[Val-Orn-Leu-Tyr-Pro-Trp-Phe-Asn-Asp-Trp] (SEQ ID NO:7);
cyclo[Butyrine-Orn-Leu-Tyr-Pro-Phe-Phe-Asn-Asp-Tyr] (SEQ ID NO:10);
cyclo[Butyrine-Orn-Leu-Tyr-Pro-Phe-Phe-Asn-Asp-Trp] (SEQ ID NO:11);
cyclo[Butyrine-Orn-Leu-Tyr-Pro-Trp-Phe-Asn-Asp-Trp] (SEQ ID NO:12);
cyclo[Val-diaminobutyric acid-Leu-Tyr-Pro-Phe-Phe-Asn-Asp-Tyr] (SEQ ID NO:13);
cyclo[Val-diaminobutyric acid-Leu-Tyr-Pro-Phe-Phe-Asn-Asp-Trp] (SEQ ID NO:14);
cyclo[Val-diaminobutyric acid-Leu-Tyr-Pro-Trp-Phe-Asn-Asp-Trp] (SEQ ID NO:15);
cyclo[Val-Orn-Isoleucine-Tyr-Pro-Phe-Phe-Asn-Asp-Tyr] (SEQ ID NO:16);
cyclo[Val-Orn-Isoleucine-Tyr-Pro-Phe-Phe-Asn-Asp-Trp] (SEQ ID NO:17);
cyclo[Val-Orn-Isoleucine-Tyr-Pro-Trp-Phe-Asn-Asp-Trp] (SEQ ID NO:18);
cyclo[Val-Orn-Alloisoleucine-Tyr-Pro-Phe-Phe-Asn-Asp-Tyr] (SEQ ID NO:19);
cyclo[Val-Orn-Alloisoleucine-Tyr-Pro-Phe-Phe-Asn-Asn-Trp] (SEQ ID NO:20);
cyclo[Val-Orn-Alloisoleucine-Tyr-Pro-Trp-Phe-Asn-Asp-Trp] (SEQ ID NO:21);
cyclo[Val-Orn-Norvaline-Tyr-Pro-Phe-Phe-Asn-Asp-Tyr]; (SEQ ID NO:22);
cyclo[Val-Orn-Norvaline-Tyr-Pro-Phe-Phe-Asn-Asp-Trp] (SEQ ID NO:23);
cyclo[Val-Orn-Norvaline-Tyr-Pro-Trp-Phe-Asn-Asp-Trp] (SEQ ID NO:24);
cyclo[Val-Orn-Cyclopropylalanine-Tyr-Pro-Phe-Phe-Asn-Asp-Tyr] (SEQ ID NO :25)
cyclo[Val-Orn-Cyclopropylalanine-Tyr-Pro-Phe-Phe-Asn-Asp-Trp] (SEQ ID NO :26);
cyclo[Val-Orn-Cyclopropylalanine-Tyr-Pro-Trp-Phe-Asn-Asp-Trp] (SEQ ID NO:27);
cyclo[Val-Orn-Norleucine-Tyr-Pro-Phe-Phe-Asn-Asp-Tyr] (SEQ ID NO:28);
cyclo[Val-Orn-Norleucine-Tyr-Pro-Phe-Phe-Asn-Asp-Trp] (SEQ ID NO:29);
cyclo[Val-Orn-Norleucine-Tyr-Pro-Trp-Phe-Asn-Asp-Trp] (SEQ ID NO:30);
cyclo[Val-Orn-Leu-p-fluorophenylalanine-Pro-Phe-Phe-Asn-Asp-Tyr] (SEQ ID NO:31);
cyclo[Val-Orn-Leu-p-fluorophenylalanine-Pro-Phe-Phe-Asn-Asp-Trp] (SEQ ID NO:32);
cyclo[Val-Orn-Leu-p-fluorophenylalanine-Pro-Trp-Phe-Asn-Asp-Trp] (SEQ ID NO:33);
cyclo[Val-Orn-Leu-Tryptophan-Pro-Phe-Phe-Asn-Asp-Tyr] (SEQ ID NO:34);
cyclo[Val-Orn-Leu-Tryptophan-Pro-Phe-Phe-Asn-Asp-Trp] (SEQ ID NO:35);
cyclo[Val-Orn-Leu-Tryptophan-Pro-Trp-Phe-Asn-Asp-Trp] (SEQ ID NO:36);
cyclo[Val-Orn-Leu-Thienylalanine-Pro-Phe-Phe-Asn-Asp-Tyr] (SEQ ID NO:37);
cyclo[Val-Orn-Leu-Thienylalanine-Pro-Phe-Phe-Asn-Asp-Trp] (SEQ ID NO:38);
cyclo[Val-Orn-Leu-Thienylalanine-Pro-Trp-Phe-Asn-Asp-Trp] (SEQ ID NO:39);
cyclo[Val-Orn-Leu-Tyr-Azetidine-2-carboxylic acid-Phe-Phe-Asn-Asp-Tyr] (SEQ ID NO:40);
cyclo[Val-Orn-Leu-Tyr-Azetidine-2-carboxylic acid-Phe-Phe-Asn-Asp-Trp] (SEQ ID NO:41);
cyclo[Val-Orn-Leu-Tyr-Azetidine-2-carboxylic acid-Trp-Phe-Asn-Asp-Trp] (SEQ ID NO:42);
cyclo[Val-Orn-Leu-Tyr-Pipecolic acid-Phe-Phe-Asn-Asp-Tyr] (SEQ ID NO:43);
cyclo[Val-Orn-Leu-Tyr-Pipecolic acid-Phe-Phe-Asn-Asp-Trp] (SEQ ID NO:44);
cyclo[Val-Orn-Leu-Tyr-Pipecolic acid-Trp-Phe-Asn-Asp-Trp] (SEQ ID NO:45)
cyclo[Val-Orn-Leu-Tyr-trans-3-Methylproline-Phe-Phe-Asn-Asp-Tyr] (SEQ ID NO:46);
cyclo[Val-Orn-Leu-Tyr-trans-3-Methylproline-Phe-Phe-Asn-Asp-Trp] (SEQ ID NO:47);
cyclo[Val-Orn-Leu-Tyr-trans-3-Methylproline-Trp-Phe-Asn-Asp-Trp] (SEQ ID NO:48);
cyclo[Val-Orn-Leu-Tyr-trans-4-Fluoroproline-Phe-Phe-Asn-Asp-Tyr] (SEQ ID NO:49);
cyclo[Val-Orn-Leu-Tyr-trans-4-Fluoroproline-Phe-Phe-Asn-Asp-Trp] (SEQ ID NO:50);
cyclo[Val-Orn-Leu-Tyr-trans-4-Fluoroproline-Trp-Phe-Asn-Asp-Trp] (SEQ ID NO:51);
cyclo[Val-Orn-Leu-Tyr-Pro-Tyr-Phe-Asn-Asp-Tyr] (SEQ ID NO:52);
cyclo[Val-Orn-Leu-Tyr-Pro-Tyr-Phe-Asn-Asp-Trp] (SEQ ID NO:53)
cyclo[Val-Orn-Leu-Tyr-Pro-p-Fluorophenylalanine-Phe-Asn-Asp-Tyr] (SEQ ID NO:54);
cyclo[Val-Orn-Leu-Tyr-Pro-p-Fluorophenylalanine-Phe-Asn-Asp-Trp] (SEQ ID NO:55);
cyclo[Val-Orn-Leu-Tyr-Pro-Trp-Phe-Asn-Asp-Tyr] (SEQ ID NO:56);
cyclo[Val-Orn-Leu-Tyr-Pro-Thienylalanine-Phe-Asn-Asp-Tyr] (SEQ ID NO:57);
cyclo[Val-Orn-Leu-Tyr-Pro-Thienylalanine-Phe-Asn-Asp-Trp] (SEQ ID NO:58);
cyclo[Val-Orn-Leu-Tyr-Pro-.β.-Phenylserine-Phe-Asn-Asp-Tyr] (SEQ ID NO:59);
cyclo[Val-Orn-Leu-Tyr-Pro-.β.-Phenylserine-Phe-Asn-Asp-Trp-] (SEQ ID NO:60);
cyclo[Val-Orn-Leu-Tyr-Pro-Phe-Tyr-Asn-Asp-Tyr] (SEQ ID NO:61);
cyclo[Val-Orn-Leu-Tyr-Pro-Phe-Tyr-Asn-Asp-Trp] (SEQ ID NO:62);
cyclo[Val-Orn-Leu-Tyr-Pro-Phe-p-Fluorophenylalanine-Asn-Asp-Tyr] (SEQ ID NO:63);
cyclo[Val-Orn-Leu-Tyr-Pro-Phe-p-Fluorophenylalanine-Asn-Asp-Trp] (SEQ ID NO:64);
cyclo[Val-Orn-Leu-Tyr-Pro-Phe-Trp-Asn-Asp-Tyr] (SEQ ID NO:65);
cyclo[Val-Orn-Leu-Tyr-Pro-Phe-Trp-Asn-Asp-Trp] (SEQ ID NO:66);
cyclo[Val-Orn-Leu-Tyr-Pro-Phe-Thienylalanine-Asn-Asp-Tyr] (SEQ ID NO:67);
cyclo[Val-Orn-Leu-Tyr-Pro-Phe-Thienylalanine-Asn-Asp-Trp] (SEQ ID NO:68);
cyclo[Val-Orn-Leu-Tyr-Pro-Phe-.β.-Phenylserine-Asn-Asp-Tyr] (SEQ ID NO:69);
cyclo[Val-Orn-Leu-Tyr-Pro-Phe-.β.-Phenylserine-Asn-Asp-Trp-] (SEQ ID NO: 70);
cyclo[Val-Orn-Leu-Tyr-Pro-Phe-Phe-Asn-Asp-p-Fluorophenylalanine] (SEQ ID NO:71):;

cyclo[Val-Orn-Leu-Tyr-Pro-Trp-Phe-Asn-Asp-p-Fluorophenylalanine] (SEQ ID NO: 72);
cyclo[Val-Orn-Leu-Tyr-Pro-Phe-Phe-Asn-Asp-Phe] (SEQ ID NO:73);
cyclo[Val-Orn-Leu-Tyr-Pro-Trp-Phe-Asn-Asp-Phe] (SEQ ID NO:74);
cyclo[Val-Orn-Leu-Tyr-Pro-Phe-Phe-Asn-Asp-Thienylalanine] (SEQ ID NO: 75);
cyclo[Val-Orn-Leu-Tyr-Pro-Trp-Phe-Asn-Asp-Thienylalanine] (SEQ ID NO: 76);
cyclo[Val-Orn-Leu-Tyr-Pro-Phe-Phe-Asn-Asp-.β.-Phenylserine] (SEQ ID NO:77); and
cyclo[Val-Orn-Leu-Tyr-Pro-Trp-Phe-Asn-Asp-.β.-Phenylserine] (SEQ ID NO:8).

5. The composition of claim 2, wherein the cyclic peptide antibiotic is loloatin A, B, or C.

6. The composition of claim 1 or 4, wherein the additional antibiotic is metronidazole or clindamycin.

7. The composition of claim 1 or 4, wherein the additional antibiotic is metronidazole.

8. A method for the treatment of a patient afflicted with rosacea, comprising topical administration to the patient of a therapeutically effective amount of a cyclic peptide antibiotic or pharmaceutically acceptable salt thereof.

9. The method of claim 8, wherein the method further comprises topical administration of an additional antibiotic or pharmaceutically acceptable salt thereof, wherein said additional antibiotic is effective against an anaerobic *bacterium*.

10. The method of claim 9, wherein the additional antibiotic is metronidazole or clindamycin.

11. The method of claim 9, wherein the additional antibiotic is metronidazole.

12. The method of claim 8, wherein the cyclic peptide antibiotic is selected from the group consisting of: loloatins; cyclic gramicidins; tyrocidins; and tyrothricins.

13. The method of claim 8, wherein the cyclic peptide antibiotic is a loloatin.

14. The method of claim 8, wherein the cyclic peptide antibiotic or pharmaceutically acceptable salt thereof is a compound of Formula (A)

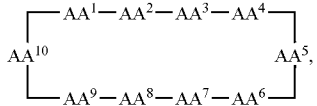

wherein $AA_1$ through $AA_{10}$ are generic symbols, each representing an amino acid residue, a salt or a derivative thereof, and each line between $AA_1$ through $AA_{10}$ represents an amide bond or an isostere thereof.

15. The method of claim 8, wherein the cyclic peptide antibiotic is selected from the group consisting of:
cyclo[Val-Orn-Leu-Tyr-Pro-Phe-Phe-Asn-Asp-Tyr] (SEQ ID NO:5);
cyclo[Val-Orn-Leu-Tyr-Pro-Phe-Phe-Asn-Asp-Trp] (SEQ ID NO:6);
cyclo[Val-Orn-Leu-Tyr-Pro-Trp-Phe-Asn-Asp-Trp] (SEQ ID NO:7);
cyclo[Butyrine-Orn-Leu-Tyr-Pro-Phe-Phe-Asn-Asp-Tyr] (SEQ ID NO:10);
cyclo[Butyrine-Orn-Leu-Tyr-Pro-Phe-Phe-Asn-Asp-Trp] (SEQ ID NO:11);
cyclo[Butyrine-Orn-Leu-Tyr-Pro-Trp-Phe-Asn-Asp-Trp] (SEQ ID NO:12);
cyclo[Val-diaminobutyric acid-Leu-Tyr-Pro-Phe-Phe-Asn-Asp-Tyr] (SEQ ID NO:13);
cyclo[Val-diaminobutyric acid-Leu-Tyr-Pro-Phe-Phe-Asn-Asp-Trp] (SEQ ID NO:14);
cyclo[Val-diaminobutyric acid-Leu-Tyr-Pro-Trp-Phe-Asn-Asp-Trp] (SEQ ID NO:15);
cyclo[Val-Orn-Isoleucine-Tyr-Pro-Phe-Phe-Asn-Asp-Tyr] (SEQ ID NO:16);
cyclo[Val-Orn-Isoleucine-Tyr-Pro-Phe-Phe-Asn-Asp-Trp] (SEQ ID NO:17);
cyclo[Val-Orn-Isoleucine-Tyr-Pro-Trp-Phe-Asn-Asp-Trp] (SEQ ID NO:18);
cyclo[Val-Orn-Alloisoleucine-Tyr-Pro-Phe-Phe-Asn-Asp-Tyr] (SEQ ID NO:19);
cyclo[Val-Orn-Alloisoleucine-Tyr-Pro-Phe-Phe-Asn-Asp-Trp] (SEQ ID NO:20);
cyclo[Val-Orn-Alloisoleucine-Tyr-Pro-Trp-Phe-Asn-Asp-Trp] (SEQ ID NO:21);
cyclo[Val-Orn-Norvaline-Tyr-Pro-Phe-Phe-Asn-Asp-Tyr] (SEQ ID NO:22);
cyclo[Val-Orn-Norvaline-Tyr-Pro-Phe-Phe-Asn-Asp-Trp] (SEQ ID NO:23);
cyclo[Val-Orn-Norvaline-Tyr-Pro-Trp-Phe-Asn-Asp-Trp] (SEQ ID NO:24);
cyclo[Val-Orn-Cyclopropylalanine-Tyr-Pro-Phe-Phe-Asn-Asp-Tyr] (SEQ ID NO:25);
cyclo[Val-Orn-Cyclopropylalanine-Tyr-Pro-Phe-Phe-Asn-Asp-Trp] (SEQ ID NO:26);
cyclo[Val-Orn-Cyclopropylalanine-Tyr-Pro-Trp-Phe-Asn-Asp-Trp] (SEQ ID NO:27);
cyclo[Val-Orn-Norleucine-Tyr-Pro-Phe-Phe-Asn-Asp-Tyr] (SEQ ID NO:28);
cyclo[Val-Orn-Norleucine-Tyr-Pro-Phe-Phe-Asn-Asp-Trp] (SEQ ID NO:29);
cyclo[Val-Orn-Norleucine-Tyr-Pro-Trp-Phe-Asn-Asp-Trp] (SEQ ID NO:30);
cyclo[Val-Orn-Leu-p-fluorophenylalanine-Pro-Phe-Phe-Asn-Asp-Tyr] (SEQ ID NO:31);
cyclo[Val-Orn-Leu-p-fluorophenylalanine-Pro-Phe-Phe-Asn-Asp-Trp] (SEQ ID NO:32);
cyclo[Val-Orn-Leu-p-fluorophenylalanine-Pro-Trp-Phe-Asn-Asp-Trp] (SEQ ID NO:33);
cyclo[Val-Orn-Leu-Tryptophan-Pro-Phe-Phe-Asn-Asp-Tyr] (SEQ ID NO:34);
cyclo[Val-Orn-Leu-Tryptophan-Pro-Phe-Phe-Asn-Asp-Trp] (SEQ ID NO:35);
cyclo[Val-Orn-Leu-Tryptophan-Pro-Trp-Phe-Asn-Asp-Trp] (SEQ ID NO:36);
cyclo[Val-Orn-Leu-Thienylalanine-Pro-Phe-Phe-Asn-Asp-Tyr] (SEQ ID NO:37);
cyclo[Val-Orn-Leu-Thienylalanine-Pro-Phe-Phe-Asn-Asp-Trp] (SEQ ID NO:38);
cyclo[Val-Orn-Leu-Thienylalanine-Pro-Trp-Phe-Asn-Asp-Trp] (SEQ ID NO:39);
cyclo[Val-Orn-Leu-Tyr-Azetidine-2-carboxylic acid-Phe-Phe-Asn-Asp-Tyr] (SEQ ID NO:40);
cyclo[Val-Orn-Leu-Tyr-Azetidine-2-carboxylic acid-Phe-Phe-Asn-Asp-Trp] (SEQ ID NO:41);
cyclo[Val-Orn-Leu-Tyr-Azetidine-2-carboxylic acid-Trp-Phe-Asn-Asp-Trp] (SEQ ID NO:42);
cyclo[Val-Orn-Leu-Tyr-Pipecolic acid-Phe-Phe-Asn-Asp-Tyr] (SEQ ID NO:43);
cyclo[Val-Orn-Leu-Tyr-Pipecolic acid-Phe-Phe-Asn-Asp-Trp] (SEQ ID NO:44);
cyclo[Val-Orn-Leu-Tyr-Pipecolic acid-Trp-Phe-Asn-Asp-Trp] (SEQ ID NO:45);

cyclo[Val-Orn-Leu-Tyr-trans-3-Methylproline-Phe-Phe-Asn-Asp-Tyr] (SEQ ID NO:46);
cyclo[Val-Orn-Leu-Tyr-trans-3-Methylproline-Phe-Phe-Asn-Asp-Trp] (SEQ ID NO:47);
cyclo[Val-Orn-Leu-Tyr-trans-3-Methylproline-Trp-Phe-Asn-Asp-Trp] (SEQ ID NO:48);
cyclo[Val-Orn-Leu-Tyr-trans-4-Fluoroproline-Phe-Phe-Asn-Asp-Tyr] (SEQ ID NO:49);
cyclo[Val-Orn-Leu-Tyr-trans-4-Fluoroproline-Phe-Phe-Asn-Asp-Trp] (SEQ ID NO:50);
cyclo[Val-Orn-Leu-Tyr-trans-4-Fluoroproline-Trp-Phe-Asn-Asp-Trp] (SEQ ID NO:51);
cyclo[Val-Orn-Leu-Tyr-Pro-Tyr-Phe-Asn-Asp-Typ] (SEQ ID NO:52);
cyclo[Val-Orn-Leu-Tyr-Pro-Tyr-Phe-Asn-Asp-Trp] (SEQ ID NO:53);
cyclo[Val-Orn-Leu-Tyr-Pro-p-Fluorophenylalanine-Phe-Asn-Asp-Tyr] (SEQ ID NO:54);
cyclo[Val-Orn-Leu-Tyr-Pro-p-Fluorophenylalanine-Phe-Asn-Asp-Trp] (SEQ ID NO:55);
cyclo[Val-Orn-Leu-Tyr-Pro-Trp-Phe-Asn-Asp-Tyr] (SEQ ID NO:56);
cyclo[Val-Orn-Leu-Tyr-Pro-Thienylalanine-Phe-Asn-Asp-Tyr] (SEQ ID NO:57);
cyclo[Val-Orn-Leu-Tyr-Pro-Thienylalanine-Phe-Asn-Asp-Trp] (SEQ ID NO:58);
cyclo[Val-Orn-Leu-Tyr-Pro-.β.-Phenylserine-Phe-Asn-Asp-Tyr] (SEQ ID NO:59);
cyclo[Val-Orn-Leu-Tyr-Pro-.β.-Phenylserine-Phe-Asn-Asp-Trp] (SEQ ID NO:60);
cyclo[Val-Orn-Leu-Tyr-Pro-Phe-Tyr-Asn-Asp-Tyr] (SEQ ID NO:61);
cyclo[Val-Orn-Leu-Tyr-Pro-Phe-Tyr-Asn-Asp-Trp] (SEQ ID NO:62);
cyclo[Val-Orn-Leu-Tyr-Pro-Phe-p-Fluorophenylalanine-Asn-Asp-Tyr] (SEQ ID NO:63);
cyclo[Val-Orn-Leu-Tyr-Pro-Phe-p-Fluorophenylalanine-Asn-Asp-Trp] (SEQ ID NO:64);
cyclo[Val-Orn-Leu-Tyr-Pro-Phe-Trp-Asn-Asp-Tyr] (SEQ ID NO:65);
cyclo[Val-Orn-Leu-Tyr-Pro-Phe-Trp-Asn-Asp-Trp] (SEQ ID NO:66);
cyclo[Val-Orn-Leu-Tyr-Pro-Phe-Thienylalanine-Asn-Asp-Tyr] (SEQ ID NO:67);
cyclo[Val-Orn-Leu-Tyr-Pro-Phe-Thienylalanine-Asn-Asp-Trp] (SEQ ID NO:68);
cyclo[Val-Orn-Leu-Tyr-Pro-Phe-.β.-Phenylserine-Asn-Asp-Tyr] (SEQ ID NO:69);
cyclo[Val-Orn-Leu-Tyr-Pro-Phe-.β.-Phenylserine-Asn-Asp-Trp] (SEQ ID NO:70);
cyclo[Val-Orn-Leu-Tyr-Pro-Phe-Phe-Asn-Asp-p-Fluorophenylalanine] (SEQ ID NO:71);
cyclo[Val-Orn-Leu-Tyr-Pro-Trp-Phe-Asn-Asp-p-Fluorophenylalanine] (SEQ ID NO:72);
cyclo[Val-Orn-Leu-Tyr-Pro-Phe-Phe-Asn-Asp-Phe] (SEQ ID NO:73);
cyclo[Val-Orn-Leu-Tyr-Pro-Trp-Phe-Asn-Asp-Phe] (SEQ ID NO:74);
cyclo[Val-Orn-Leu-Tyr-Pro-Phe-Phe-Asn-Asp-Thienylalanine] (SEQ ID NO:75);
cyclo[Val-Orn-Leu-Tyr-Pro-Trp-Phe-Asn-Asp-Thienylalanine] (SEQ ID NO:76);
cyclo[Val-Orn-Leu-Tyr-Pro-Phe-Phe-Asn-Asp-.β.-Phenylserine] (SEQ ID NO:77); and
cyclo[Val-Orn-Leu-Tyr-Pro-Trp-Phe-Asn-Asp-.β.-Phenylserine] (SEQ ID NO:8).

16. The method of claim 8, wherein the cyclic peptide antibiotic is loloatin A, B, or C.

* * * * *